United States Patent [19]

Spalten

[11] 4,021,916
[45] May 10, 1977

[54] DENTAL DOWEL PIN POSITIONER

[76] Inventor: Robert Spalten, 745 Fifth Ave., New York, N.Y. 10022

[22] Filed: Aug. 20, 1975

[21] Appl. No.: 606,323

[52] U.S. Cl. ............................................. 32/11
[51] Int. Cl.² .................................... A61C 13/00
[58] Field of Search ................................. 32/11

[56] References Cited

UNITED STATES PATENTS

| | | | |
|---|---|---|---|
| 1,696,422 | 12/1928 | Thayer | 32/11 |
| 3,815,236 | 6/1974 | Cooper | 32/11 |
| 3,832,777 | 9/1974 | Tinder | 32/11 |

Primary Examiner—Robert Peshock

Attorney, Agent, or Firm—Harry Ernest Rubens

[57] ABSTRACT

A dental appliance for maintaining axis parallelism of dental dowel pins when positioning replicas of teeth taken from impressions in a model of the mouth, which employs a plate, connected pivoting links, or a rail, having a plurality of apertured seats for mounting the dowel pins therein in positions conforming to the configurations of the teeth and for maintaining axis parallelism of the dowel pins, said apertured seats being permanently mounted to each other in predetermined transverse positions, to provide a simplified structure for locating the mounted dowel pins with respect to the impressions of the teeth.

7 Claims, 10 Drawing Figures

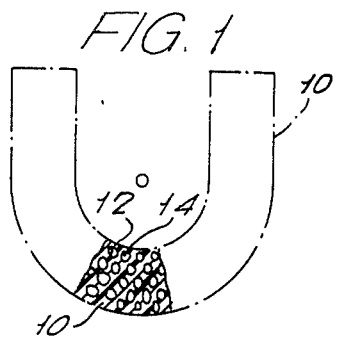
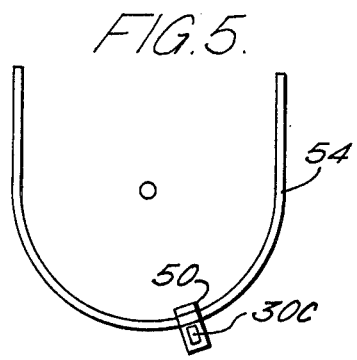
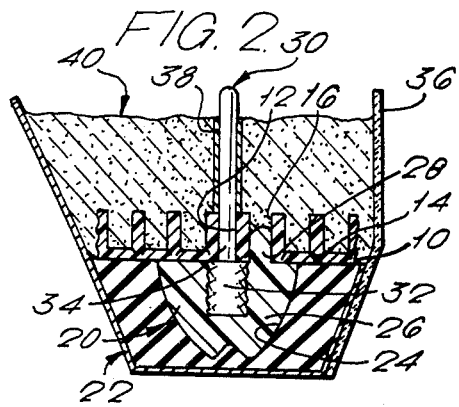
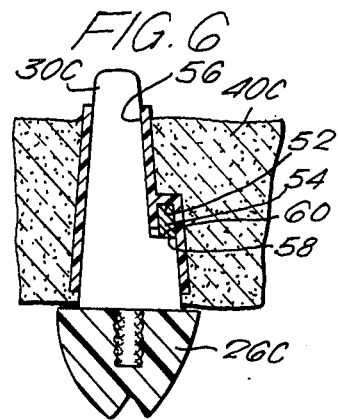
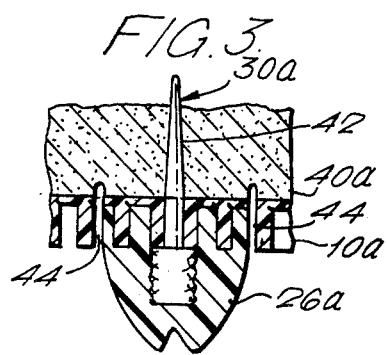
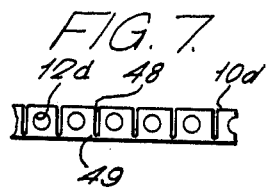
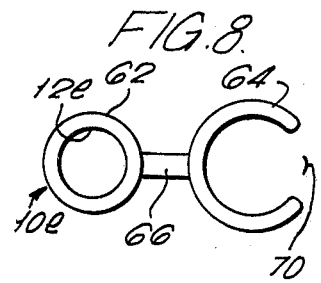
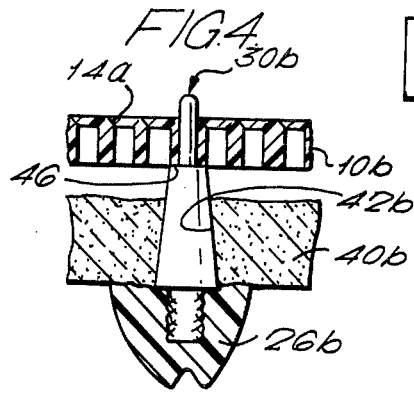
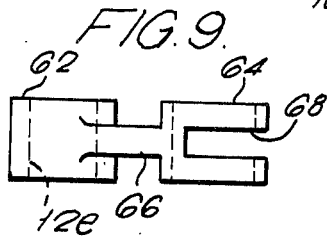
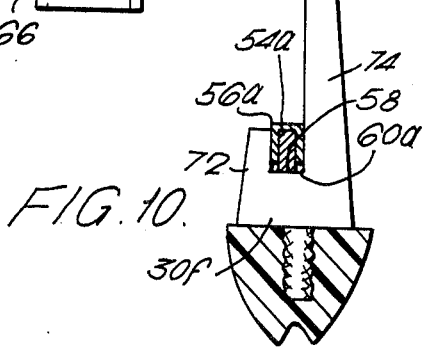

DENTAL DOWEL PIN POSITIONER

This invention relates to dental appliances and, more particularly, to apparatus for precisely supporting and positioning replicas of the teeth in the model of the mouth.

The present invention is a further improvement of the dental dowel pin positioning apparatus shown in my earlier U.S. Pat. Nos. 2,851,728 and 3,226,827.

A dental dowel pin is an elongated rod mounted to a tooth replica formed from an impression material of the teeth of the mouth. The dowel pin, when properly positioned, is removably embedded in a supporting base material for establishing the exact tooth position with respect to the adjacent teeth in the mouth. Thus, when the individual replicas and dowel pins are removed for preparing crowns, bridgework and other forms of mouth rehabilitation, the prepared construction may be accurately relocated in the supporting base with respect to the adjacent teeth.

The present object of the invention is to provide a simple construction to add axis parallelism to the dowel pins, so that they can be removed individually or in multiple units and replaced without loss of their exact relative positions.

Another object is to provide an inexpensive construction for achieving dowel pin axis parallelism which may be embedded permanently in the supporting base of the model of the mouth, or permanently affixed to the tooth replica.

Still another object is to provide a construction for achieving dowel pin axis parallelism without loss of the seating accuracy accomplished by the construction shown in my U.S. Pat. No. 2,854,728 or the electrical signalling feature disclosed in U.S. Pat. No. 3,226,827.

Other objects are to achieve axis parallelism for the dowel pins, when positioned on the conductor employed in my earlier construction, to signal electrically, dowel pin seating accuracy.

I accomplish these and other objects of my invention, and obtain my new results, as will be apparent from a consideration of the following description, and claims, and from the apparatus illustrated in the drawings, in which:

FIG. 1 is a plan view of an apertured axis positioning plate or positioner, shown in fragmentary form, the complete outline shown in dot-dash which may be used to achieve pin parallelism;

FIG. 2 is a sectional view of a final assembled construction with the apertured plate embedded in the supporting base material;

FIG. 3 is a sectional view of a final assembled construction with the apertured plate permanently attached to the dowel pin and tooth replica;

FIG. 4 is a sectional view of an assembly with the apertured plate in removable position;

FIG. 5 is a plan view of a conductor rail with associated sleeve for achieving axis parallelism;

FIG. 6 is a sectional view of the sleeve, rail, and affixed replica;

FIG. 7 is a plan view of an apertured hinged positioner;

FIGS. 8 & 9 are plan and side view of a snap-on hinged positioner;

FIG. 10 is a modification of the conductor rail and associated dowel pin.

The invention may be carried out by employing a U-shaped apertured plate or positioner 10 shown in FIG. 1 which generally follows the peripheral position of the teeth in the mouth.

The aperture constituting the seats 12, may be cylindrical in shape, or slightly conical if a more accurate longitudinal seating position is desired along the axis of the apertures. The bottom of the apertures may be closed, but provided with weakened walls, as at 14 in FIG. 2 to permit a dowel pin to push out the weakened section for entrance therein.

The various steps employed in preparing precision splints, indirect inlays, crowns, large span bridgework and other reconstructions in the mouth are illustrated in FIG. 2.

A rubber impression 20 is made of the teeth in the mouth, which is supported by a tray 22.

The apertured plate 10 is supported over the teeth impressions 24 and dowel pins 30 are inserted into apertures 12 in positions as closely conforming to the center of each impession 24 of the teeth as is possible, forcing out the weakened closure 14 which is located in the aperture. The aperture plate may be made of transparent plastic to facilitate locating the pins therein, and the apertures should be as close together as is possible consistent with the structural strength required in the plate.

The pins are shaped to provide a knurled stem 32 for embedding in the tooth replica 26 as will be hereinafter described. A cylindrical neck portion 34 is positioned above the stem for seating in the apertures 12 of the plate. A relatively tight sliding fit is needed to insure accuracy in alignment and to keep the positioned pins from falling out during the positioning operation.

The tooth impression 24 is filled with a die material such as an epoxy material, in its fluid state, and the knurled stems 32 of the dowel pins in position on the positioning plate, is inserted therein. When the replica 26 of the tooth hardens, the dowel pins are permanently attached thereto.

A wax box 38 is built up around the impression tray to support the base material which is poured into the box over the dowel pins.

The base material or stone 40, made of plaster of paris, is then formed about the pins leaving a portion of the pin free of the stone for applying pressure thereto, to free the pin from the stone. To facilitate removal, the dowel pins may be coated with a separating fluid to which the stone will not adhere. A plastic sleeve 38 may be mounted around the dowel pin to enable the pin to slide freely from the cast stone.

To prevent any rotation of the dowel pins in the stone openings, an additional opening 16 adjacent to the neck 34 of the pin, may be formed through a weakened section to provide dual pins for each replica, when the replica 26 is formed, a portion of the resin may be pressed through the aperture 16 of the plate 10 to form an auxilliary pin 28 which, together with the neck 34, will orient the replica about the stone cast 40. As is apparent in this illustration, the stone 40, and the plate 10 are unified, and the dowel pin 30 and associated replica 26 are removed from the stone, as a unit when the tray 22 with the rubber impression material, and the wax box are removed.

In place of the replica formed pin 28, two dowel pins may be used for each tooth replica or group or replicas. This will automatically orient the replicas in the proper location with respect to the cast stone. This will eliminate the conventional step of flattening one side of the dowel, to orient the dowel pin and stone.

In FIG. 3, the positioning plate 10a is made a part of the dowel pin 30a, and replica 26a assembly. The dowel pin is tapered, as at 42 to facilitate removal from the stone 40a. Saw cuts 44 allows the individual replica 26a and associated dowel pin 30, to be removed from the stone, the positioning plate 10a being severed to permit such removal.

FIG. 4 illustrates a desirable construction, in that the positioning plate 10b is not incorporated into the stone 40b, as is shown in FIG. 2, or unified with the dowel pin 30b, as is illustrated in FIG. 3.

In this form the dowel pin is provided with a shoulder 46, which prevents the positioning plate from contacting the stone 40b. The dowel pin below the shoulder is tapered, as at 42b, to facilitate removal, with the replica 26b, from the stone.

The electrical signalling feature may be incorporated in the modification shown in FIGS. 5 & 6. This employs an axis positioning plastic sleeve 50 having a transverse aperture 52 through which is mounted a rail 54 used for maintaining the axis of each sleeve in exact parallelism with each other as well as providing conductivity between the adjacent dowel pins as will be hereinafter described.

Only one sleeve is illustrated although as many sleeves are provided, as there are tooth impressions to be filled.

The sleeves have longitudinal passageways 56 conforming to the contours of the surfaces of the dowel pin 30c when seated therein.

The transverse rail passageway 52 of the sleeve is open as at 58 so that a stop surface 60 of the dowel pin may electrically contact the exposed side of the rail 54 when the dowel pin is fully seated in the sleeve.

To this end the edge surfaces of the dowel pin and the inner surfaces of the sleeve are similarly tapered to provide an exact seat when the electrical contact between rail and dowel pin is made.

The stone 40c completely encloses the sleeve and rail 54, except for the ends thereof which extend through the wax box not here shown, to permit connection to an electrical circuit containing a light which will glow when the circuit is completed by touching the exposed end of the pin 30c, if properly seated.

The dowel pins here illustrated are thin to permit movement over rail 54. The rail itself is thin, as shown in FIG. 6, to facilitate movement of the sleeve and pin over the rail to obtain the best location for connecting the dowel pin to its replica 26c. The rail may be made of conducting metal that can be bent into the desired tooth configuration.

I can obtain the electrical signalling feature when using the positioning plate by employing a conductive mesh screen like that illustrated in FIG. 5 of my U.S. Pat. No. 3,226,827, which is deposited over the dowel pins and in electrical contact therewith, before the stone is formed. The stone will embed the screen in contact with each dowel pin so that the dowel pins are fully seated; an electrical signal may be used to confirm the contact.

In FIG. 7, there is illustrated a flexible form of positioner 10d made of plastic wherein each apertured seat 12d is separated from its adjacent seat by a slot 48 which forms a plastic hinge 49 to link the adjacent seats into an axis maintaining seat for the adjacent pins. The plastic hinge permits the positioner 10d to be flexed into a curved position, when desired to position the dowel pins which are inserted into the seat, as illustrated in FIG. 4 for example, into position for mounting in a tooth impression.

The plastic used for making containers and integrally formed lids used commercially for many products, may be used for this modification.

A metal strip that can be easily bent but which will retain its bent position may be mounted to the hinged side of positioner 10d to maintain the flexed position and to give a seating signal.

In FIG. 8, there is illustrated another type of flexible positioner 10e, comprising a series of links, each provided with a cylindrical section 62 at one end of the link, each section containing a dowel pin positioning seat 12e. At the other end of the link 10e, a C-shaped clip-like cylindrical section 64 is formed having an internal diameter for snapping another link end similar to 62 therein. The two end sections are joined together by a bar 66.

The C-shaped clip 64 is slotted as at 68 to permit the bar 66 of a similar clip to pivot into the slot, if it is desired to move one inserted dowel pin seated in one link angularly with respect to an adjacent pin seated in the nested link.

The C-shaped cylindrical section may need a mouth opening 70, slightly larger than the width of the bar section, which will permit longitudinal insertion of one end 62 into a C-shaped end of an adjacent link. The inner diameter of the C-shaped end should be slightly smaller than the outside diameter of the end 62, to permit a resilient gripping about the inserted end. A resilient plastic which is shape retaining is desirable as the material for the links.

Another form of electrical signalling dowel pin is shown in FIG. 10. The rail 54a is shown provided with an insulating U-shaped sleeve 56a, which is open on the side 58, exposing the rail.

The flat dowel pin 30f is shown provided with two legs 72 and 74, allowing the intermediate stop surface 60a to engage the rail, when seated. The inner surfaces of the two legs are parallel to fit snugly over the rail while the outer edges are tapered to facilitate removal from the stone, not shown.

The apertures in positioner 10 may be about 2 mm. in diameter and about 2 mm. in thickness. This will provide adequate support with accurately seated dowel pins to maintain axial integrity needed for precisely supporting and positioning teeth replicas in a model of the mouth. However, the aperture of the positioner in the form shown in FIG. 4, may be reduced to ½ mm. in diameter or less, and the holes brought closer together in the plate since it need take only the head of the dowel pin, which may be minimal in size.

The material of the plate positioner may be transparent styrene, which is inexpensive for one-time use, if desired.

The dowel pin and associated tooth replica may be removed from the stone as a unit and accurately reseated in the stone cast by pressing it into the cast until electrical contact is established with the rail in the modification shown in FIG. 5, 6 and 10, and when a screen is used in the other constructions. This can occur only when the dowel pin is properly seated in the sleeve. Thus, the sleeve, which has been axially aligned to produce parallelism with the rail, will reestablish the proper axis position to enable accurate reproductions in the mouth.

The invention is characterized by deliberate selection of a predetermined number of dowel pin supporting positions, rather than provide an infinite number of positions, which will permit each dowel pin to be centered in the exact center of each tooth impression. The selection of predetermined positions, as, for instance, the distance between centers of the apertured seats in the positioning plate, or the movement of the sleeves on the fixed shape of the conducting rail, has been found sufficient for general dental use, and justifies the simple design as against a dental appliance which allows an exact centering of the dowel pins in axial parallelism, but requires a complicated mechanism for freeing the positioning means for each dowel pin, and thereafter locking each dowel pin seat into fixed relationship to each other.

The positioning means, or positioner, can thus be a plate with closely spaced apertues, a connecting link which is either flexibly connected or is capable of being bent; or a rail provided with special dowel pin seating means.

I have in the foregoing described various forms of the invention. However, it will be understood that other embodiments are possible without departing from the invention, and it is intended that all matter contained in the description and shown in the drawing shall be interpreted as illustrative, and not in a limiting sense.

What I claim is:

1. In a dental appliance for maintaining axis parallelism of dental dowel pins when positioning replicas of the teeth taken from impressions in a model of the patient's mouth, the combination of dowel pins and a positioning means having a plurality of apertured seats for mounting the dowel pins therethrough in positions conforming to the configuration of the patient's teeth; and apertured means for maintaining axis parallelism of the dowel pins to each other; and means for seating each dowel pin in the longitudinal axis of a replica; said apertured seats being mounted to each other in predetermined transverse relationships to provide a connected unitary structure at all times.

2. The dental appliance of claim 1, wherein the positioning means can be shaped into the desired configuration.

3. The dental appliance of claim 1, wherein the positioning means comprises a plurality of connecting links.

4. The dental appliance of claim 1, wherein the positioning means and the dowel pins are embedded in a cast material.

5. In the dental appliance of claim 1 a dowel pin provided with a seat for engaging the positioning means in a predetermined longitudinal position with respect thereto.

6. The method of employing the dental appliance of claim 1, which comprises the step of inserting a dowel pin into a seat on the positioning means which corresponds to the nearest position of the seat which will support the dowel pin over the tooth impression in the mouth model.

7. The method of claim 6, in which the positioning means and seated dowel pins are embedded in a layer of hardenable casting material, permanently affixing the positioning means therein.

* * * * *